(12) United States Patent
Lim et al.

(10) Patent No.: US 6,661,938 B2
(45) Date of Patent: Dec. 9, 2003

(54) OPTICAL MICRO-CAVITY SENSORS

(75) Inventors: Desmond R. Lim, Cambridge, MA (US); Anuradha Agarwal, Weston, MA (US); Lionel C. Kimerling, Concord, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/963,026

(22) Filed: Sep. 25, 2001

(65) Prior Publication Data

US 2002/0097947 A1 Jul. 25, 2002

Related U.S. Application Data

(60) Provisional application No. 60/235,008, filed on Sep. 25, 2000.

(51) Int. Cl.[7] ............................................. G02B 6/00
(52) U.S. Cl. ..................................... 385/12; 385/129
(58) Field of Search ........................... 385/12, 129, 131

(56) References Cited

U.S. PATENT DOCUMENTS

| 4,873,691 A | * | 10/1989 | Uomi et al. | 372/20 |
|---|---|---|---|---|
| 5,437,840 A | | 8/1995 | King et al. | 356/136 |
| 5,766,956 A | | 6/1998 | Groger et al. | 514/343 |
| 5,848,088 A | * | 12/1998 | Mori et al. | 372/50 |
| 5,978,401 A | * | 11/1999 | Morgan | 372/50 |
| 6,320,991 B1 | * | 11/2001 | Challener et al. | 385/12 |
| 6,349,106 B1 | * | 2/2002 | Coldren | 372/50 |

FOREIGN PATENT DOCUMENTS

| WO | WO 99/37996 | 7/1999 | .................. 385/12 |
|---|---|---|---|
| WO | WO 00/17401 | 3/2000 | |

OTHER PUBLICATIONS

Stamm et al. "Integrated optical difference interferometer as immunosensor," *Elsevier Science S. A.* 1996; p. 203–207.
Foresi et al. "Photonic–bandgap microcavities in optical waveguides" *Nature.* Nov. 13, 1997; vol. 390.

* cited by examiner

*Primary Examiner*—Hung N. Ngo
(74) *Attorney, Agent, or Firm*—Samuels, Gauthier & Stevens, LLP

(57) ABSTRACT

An integrated optical sensor using optical waveguide microcavity resonators. Using a laser and a detector it is possible to detect changes in the position of the resonance position, in wavelength or frequency, of one or more modes of the resonator. The change in resonance can be made dependent on chemicals, which have been adsorbed by chemically or biologically sensitive material provided in close proximity to the resonator.

13 Claims, 2 Drawing Sheets

OPTICAL MICRO-CAVITY SENSORS

PRIORITY INFORMATION

This application claims priority from provisional application Ser. No. 60/235,008 filed Sep. 25, 2000.

BACKGROUND OF THE INVENTION

The invention is in the field of optics, specifically in using the resonance of optical waveguide micro-resonators as chemical, biological or physical sensors.

Optical sensors can be broadly categorized, in decreasing order of size into free spaced sensors, fiber based sensors and integrated optics sensors. The main advantages of integrated optics sensors are that it is possible to fabricate them using the well established traditional silicon integrated processing, and that is possible to make very small but high functionality devices with low cost. There are, however, difficulties with the integrated optics approach, the primary one being that current devices are large and packaging the non-integrated components such as lasers can be expensive.

There have been many implementations of integrated optical waveguide sensors. However, these prior art has focused primarily on straight waveguides with using a differential TE/TM measurement on waveguides. Currently, the most sensitive integrated optics sensors use a differential TE/TM method. The principle idea is to use a waveguide that is coated with a thin layer of material and that has a strong affinity for the substance to be detected. If the material to be detected is present, it will stick to the binding layer of the material and the difference in interaction of the evanescent fields of the TE and TM modes can be measured as a difference in phase, by interfering the TE and TM modes together at the output facet.

In addition, the waveguides that have been used have primarily been slab waveguides, since this differential TE/TM method is so sensitive that scattering due to sidewall roughness would result in a severe reduction in efficiency. These TE/TM differential methods also suffer from the fact that a long interaction is needed and the lack of horizontal confinement in the slab waveguides. These two facts make these methods large and difficult to integrate on a large scale. Another drawback of this method is the need for a stabilization scheme to prevent the sensor from being completely dominated by environmental changes.

SUMMARY OF THE INVENTION

The invention provides an optical micro-resonator used as a sensor. Using a laser and a detector it is possible to detect changes in the position of the resonance position, which would in turn be dependent on the chemicals, which have been adsorbed by chemically or biologically sensitive material.

Integrated optical difference interferometers have been widely studied in the literature. These devices take advantage of the difference in interaction between the TE and TM modes and a chemical or biological agent on the surface of the waveguide. Using a micro-resonator with a TE and a TM mode, this same effect can be applied to a micro-resonator. With a high Q (~10000) resonator the effective path length can be made to be the order of 1 cm, and the sensitivities are very high. The invention utilizes optical waveguide micro-cavity resonators as sensors and further methods to improve the usability and cost. In addition, a control resonator can be fabricated close by and any environmental changes can be monitored. Resonators make very good sensors. For example, small amounts of chemicals or biological compounds bound to the surface of a micro-cavity can lead to changes in the effective index which in turn leads to large changes in the position of a resonance peak which may be easily observed. Thus, these resonators can be used as very sensitive sensors. Scanning a device for a resonance requires either a white light source with a spectrometer or a wavelength tunable source, both of which are expensive. In accordance with the invention, dithering the position of the resonance and using a single wavelength narrow band laser source to excite the wavelength cavity is explored. When the resonance of the resonator overlaps with the wavelength of emission, the output power that can be measured by a detector will drop. If there is an external change to the resonator due to the change in what is being sensed, the resulting peak shift will be overlapped with the dithering of the resonance position. This may be detected using electronics. The dithering of the resonator can be based on thermo-optic, electro-optic or some other means.

Furthermore, all the techniques, which have been developed from the slab waveguide differential TE/TM sensors, can be easily applied to micro-resonator sensors by simply studying the difference in position of the TE and TM resonances. Thus, when chemicals or biological compounds bind to the surface of the resonator, the TE and TM modes will respond differently. This leads to an effect index change that can be picked up as shifts in the resonance line spectrum.

One of the drawbacks of the resonance technique is that the spectral response is required. The implication being that a tunable laser or a spectrometer is required. However, this is very expensive and difficult to integrate. Furthermore, tunable lasers and spectrometers with large spectral ranges are usually not robust. Hence, it is essential to come up with a scheme to eliminate this problem. The invention provides a resonance dithering method, in which, the resonator line position is changed using an external tuning mechanism like thermal tuning. Such a method would allow the spectrum to be obtained without a tunable laser or spectrometer.

DETAILED DESCRIPTION OF THE INVENTION

Figure 1:
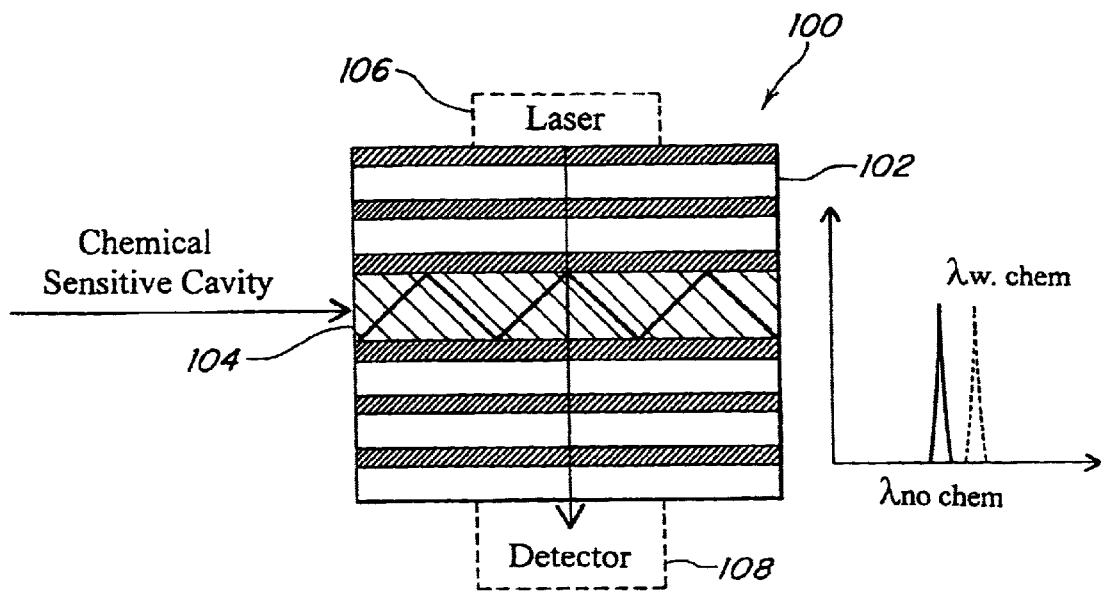
FIG. 1 is a schematic block diagram of an optical micro-cavity resonator sensor and measured response in accordance with an exemplary embodiment of the invention.

In accordance with the invention, an optical micro-cavity resonator is used as a sensor. Optical micro-cavity resonators are small resonators with sizes on the order of 0.1 micrometer to 1 millimeter. Examples of such waveguide-based micro-resonators include, optical micro-ring resonators, and one-dimensionally periodic photonic band gap waveguide structures. FIG. 1 is a schematic block diagram of an optical micro-cavity resonator sensor 100 and measured response in accordance with an exemplary embodiment of the invention. The sensor includes a multi-layered one-dimensionally periodic photonic band gap structure 102 with a chemically sensitive cavity 104, and thus is configured as a chemical sensor. Light from a light source 106 is incident from the top of the sensor, and is collected at the other end of the device (or possibly in reflection mode) by a detector 108. The light source may either be a tunable laser or a white light source. In the case of the laser, the light is detected using a standard detector, while in the case of a white light source, the light needs to be detected by a spectrometer. In both cases, a device is needed to control of the input polarization. An example of such a device is a polarization controller, which may be integrated or may be external to the waveguide chip. A biological or chemical binder can be attached to the surface of or close to the core of the micro-resonator cavity 104. The cavity 104 has to be exposed, and made sensitive to the target that needs to be detected The resonance position of a particular cavity mode is measured before during and after the exposure to the unknown substance. If the substance, which is to be detected, is present in the unknown substrate, the substance binds close to the core of the waveguide. The evanescent tails of each waveguide mode will interact with this substrate. This in turn results in a difference in the change in the resonance line position, which may be calibrated against concentration of the targeted substance. Thus, a sensitive measurement can be made.

In general, all micro-cavity optical resonators may be used as sensors in the same way. Some method of making the micro-resonator, its surface, or its immediate surroundings sensitive to the material to be detected is needed. Together with micro-ring resonators and other micro-cavity resonators, the micro-resonators should be very small sensitive and efficient sensors. These resonators can be built with Qs of up to 10,000, which correspond to effective path lengths on the order of 1 cm. The key to the sensitivity of such a device is a high Q device. Q is defined as the quality of the resonator and is inversely proportional to the width of the resonance. As the Q of the device increases, the resonance narrows and the device becomes more sensitive. One of the biggest advantages of this invention is the fact that a control micro-resonator can be built adjacent to the device under test and environmental changes can be accounted for. Thus, to exploit the full potential of this invention a compact high Q micro-resonator cavity must be fabricated.

In an exemplary embodiment of the invention, micro-resonators are formed from high index contrast waveguides. High index difference waveguides, typically have index difference between the core and cladding equal to or larger than 0.3 and can be made in several different geometries, including channel waveguides and rib waveguides. A channel waveguide is a dielectric waveguide whose core is surrounded by a cladding that is composed of a material or materials with refractive indices lower than that of the core, and wherein the peak optical intensity resides in the core. High index difference waveguides can be defined in other waveguide geometries including a rib waveguide. A rib waveguide is a dielectric waveguide whose core is surrounded by a cladding that is composed of materials of which at least one has the same refractive index as that of the core. In waveguide configurations that are difference from a channel waveguide, a high index difference waveguide is defined as one that has a mode-field size similar to that of a high index difference channel waveguide (within 50% difference in cross-sectional area). In these waveguides, cladding is defined as a region where the evanescent field of optical modes exists.

Small micro-resonators, formed from high index difference (difference in the refractive indices of core and cladding) waveguide geometries are particularly useful since their free spectral ranges are large and their physical dimensions are small. The large free spectral range (the distance between two consecutive resonance positions) coupled with a large Q allows a high dynamic range sensor to be fabricated. Another advantage of high index difference micro-resonators is the ability to pack a large number of these resonators a single carrier substrate. As a result it is possible to use multiple micro-resonators on a single chip to sense multiple chemicals, biological materials or physical effects; provided one designs each micro-resonator to respond in a special way to each target to be sensed.

A further enhancement of this invention is possible if one exploits the differential TE/TM optical sensing methods, which have been conventionally studied. However, instead of using a straight or slab waveguide, a micro-resonator cavity is used as in the present invention. The principle of operation of differential TE/TM methods allows one to increase the sensitivity of the sensor shown in FIG. 1. In this case, the difference in positions between the TE and TM modes is the measured parameter from which the concentrations of the material to be detected is determined. Using a differential method makes the measurement more efficient. In addition, the sensor can be made even more stable by building an otherwise identical control resonator adjacent to the sensor. Any drifts in the environment can be eliminated using this method. This effectively reduces the size of the device and allows for more effective environmental control. Again, the key to the sensitivity of such a device is a high Q device.

Figure 2:
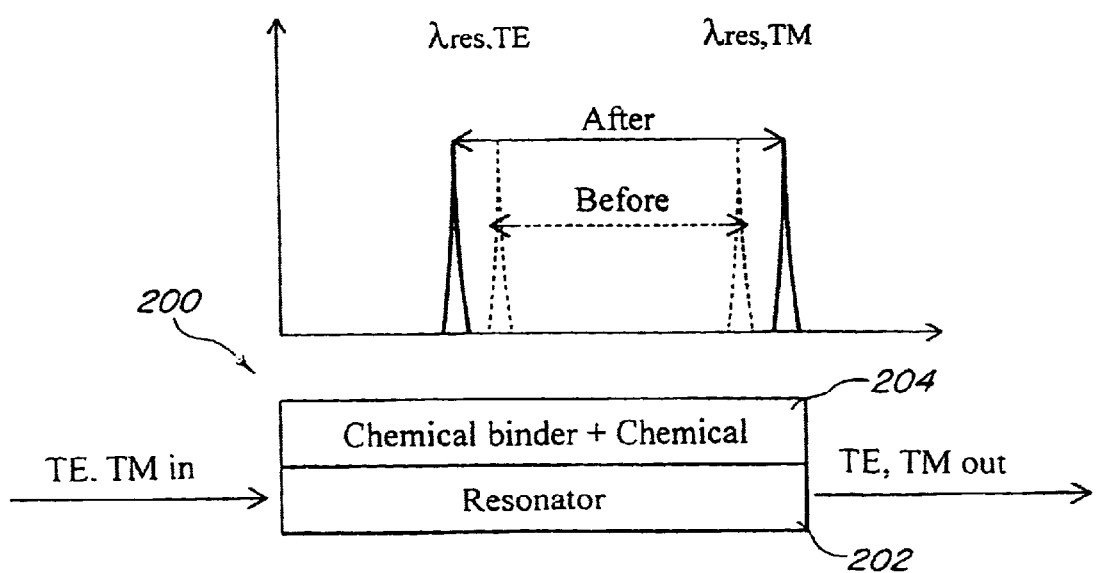
FIG. 2 is a schematic block diagram of a differential TE/TM micro-resonator cavity sensor and measured response in accordance with an exemplary embodiment of the invention.

FIG. 2 is a schematic block diagram of a differential TE/TM micro-resonator cavity sensor 200 and measured response in accordance with an exemplary embodiment of the invention. An optical waveguide micro-resonator cavity 202 that has a single mode in TE and a single mode in TM is first fabricated. A biological or chemical binder 204 is then attached to the surface of or close to the core of the micro-resonator cavity 202. A tunable laser source or a white light source is used as the light source for the device. If a tunable laser source is used, the output is detected using an optical detector. If a spectrometer is used, the output is detected using a spectrometer. In both cases, a device is needed to control of the input polarization is important. An example of such a device is a polarization controller, which may be integrated or may be external to the waveguide chip.

The resonance positions of the TE mode and the TM mode are both measured before during and after the exposure to the unknown substance. If the substance, which is to be detected, is present in the unknown substrate, the substance binds close to the core of the waveguide. The evanescent tails of each waveguide mode will interact differently with this substrate. This in turn results in a difference in the change in the resonance line position for both the TE and TM modes. Thus, the difference in line position can be calibrated against concentration of the targeted substance and a sensitive measurement can be made.

Another exemplary embodiment of the invention involves resonator based sensors by dithering the resonance position. The operation of this technique requires a tuning method for the micro-resonator. In the invention, the micro-cavity resonator is tuned on chip. There are several methods to do this. When the resonance of the resonator overlaps with the wavelength of emission the output power, which can be measured by a detector, will drop. If there is an external change to the resonator due to the change in what is being sensed, the resulting peak shift will be overlapped with the dithering of the resonance position. This may be detected using electronics. The dithering of the resonator can be thermo-optic, electro-optic or some other means. With this dithering it is possible to eliminate the tunable laser or the spectrometer, both of which are expensive and not as robust as completely monolithic schemes.

A differential TE/TM sensor micro-resonator cavity sensor would have its response measured by dithering the resonance by a tuning as opposed to using a tunable laser. In this case, instead of using a tunable laser or a spectrometer to provide the spectrum of the resonator, the fact that the resonator has a high Q is exploited. By tuning the resonator and fixing the source, it is possible to map out any physical changes to the resonator. Eliminating the laser or spectrometer reduces cost at the expense of increase complexity.

Figure 3:
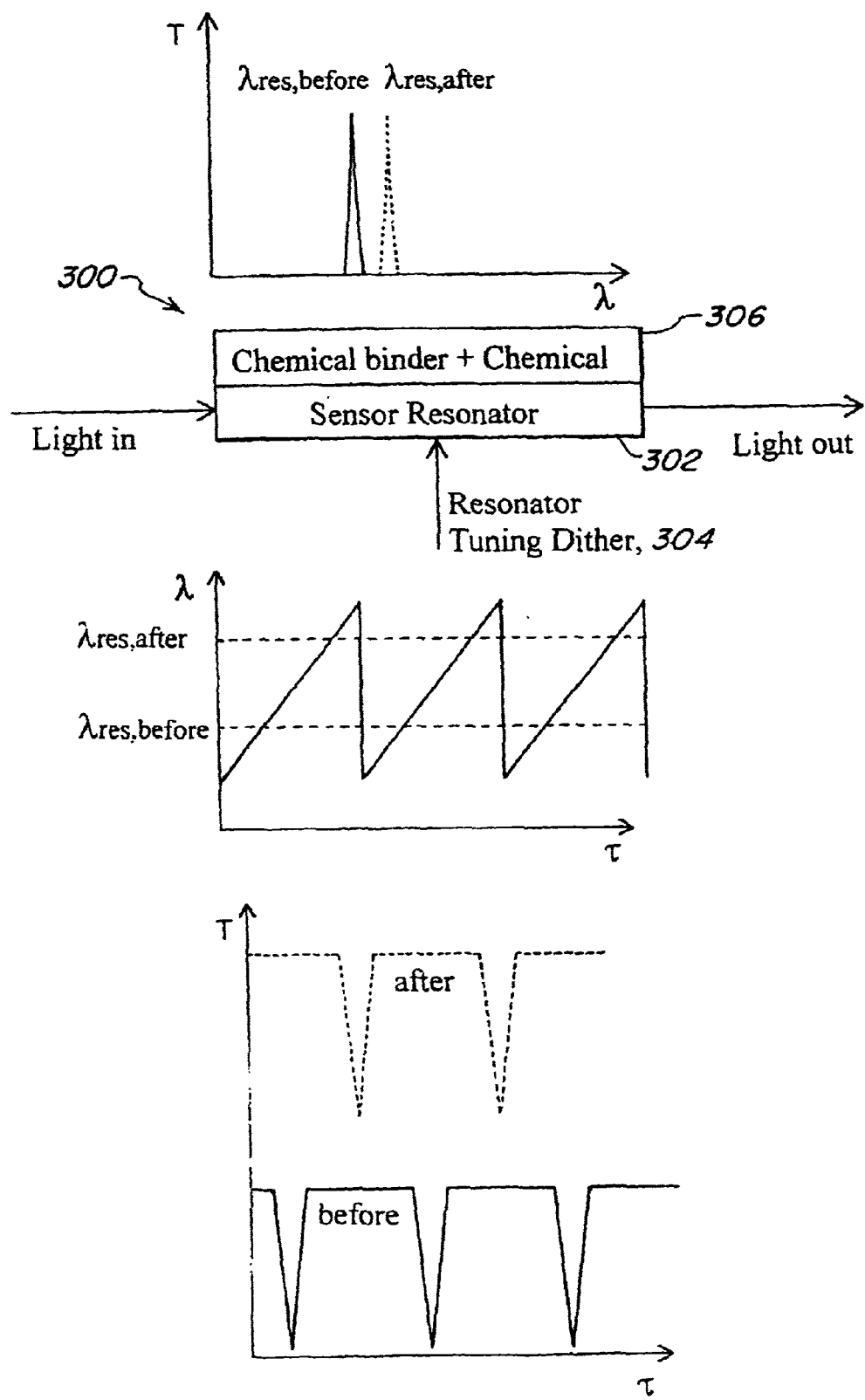
FIG. 3 is a schematic block diagram of a differential TE/TM micro-cavity sensor and measured response in accordance with an exemplary embodiment of the invention.

FIG. 3 is a schematic block diagram of a differential TE/TM micro-cavity sensor 300 and measured response in accordance with an exemplary embodiment of the invention. A micro-resonator cavity 302 is fabricated with a tuning mechanism 304, which is either monolithically integrated onto the chip or is packaged onto the chip. A biological or chemical binder 306 is then attached to the surface of or close to the core of the micro-resonator cavity 302.

The light source is a single wavelength laser source and the detector is placed at the output waveguide. If the laser is left on and the resonator is tuned over a sufficiently large range, the resonance of the cavity will at some point coincide with the input laser wavelength. It is easy to determine the amount of tuning that is required to achieve resonance with electronics. If the sensor is now placed in a substrate, which has the substance to be detected, the substance will bind close to the core of the waveguide and change the effective index of the waveguide. Thus, the amount of tuning required to achieve resonance will change. This difference can then be evaluated using electronics. If the difference in tuning is calibrated with the concentration of the substance binding at or near to the core of the waveguide, this method will be extremely sensitive.

Although the present invention has been shown and described with respect to several preferred embodiments thereof, various changes, omissions and additions to the form and detail thereof, may be made therein, without departing from the spirit and scope of the invention.

What is claimed is:

1. An integrated optical sensor comprising:
   an optical planar waveguide micro-resonator device; and
   means for measuring change in resonance position, in wavelength or frequency, of one or more modes of said micro-resonator device, wherein the difference in position, in wavelength or frequency, of two or more modes is measured.

2. The sensor of claim 1, wherein said means for measuring comprises a tunable laser source.

3. The sensor of claim 1, wherein said means for measuring comprises a white light source coupled with a spectrometer.

4. The sensor of claim 1, wherein said means for measuring comprises a light source and a detector that are hybridly or monolithically integrated with said micro-resonator device.

5. The sensor of claim 1 further comprising a chemically or biologically sensitive layer in close proximity to said micro-resonator device.

6. The sensor of claim 1 when integrated with more than one other sensor on the same chip.

7. An integrated optical sensor comprising:
   at least one optical waveguide micro-resonator device; and
   means for measuring change in resonance position, in wavelength or frequency, of one or more modes of said at least one micro-resonator devices a sensor, said means including a light source, wherein the change in position of wavelength is determined by tuning said micro-resonator device and keeping the frequency of said light sourced fixed.

8. The sensor of claim 6, wherein the difference in position, in wavelength or frequency, of two or more modes is measured.

9. The sensor of claim 6, wherein said means for measuring comprises a tunable laser source.

10. The sensor of claim 6, wherein said means for measuring comprises a white light source coupled with a spectrometer.

11. The sensor of claim 6, wherein said means for measuring comprises a light source and a detector that are hybridly or monolithically integrated with said micro-resonator device.

12. The sensor of claim 6 further comprising a chemically or biologically sensitive layer in close proximity to said micro-resonator device.

13. The sensor of claim 1 when integrated with more than one other sensor on the same chip.

* * * * *